United States Patent
Wyatt

(10) Patent No.: US 7,642,384 B2
(45) Date of Patent: *Jan. 5, 2010

(54) PROCESS FOR PREPARING CYCLOHEXANONE AND CYCLOHEXANOL

(75) Inventor: Larry Walker Wyatt, Augusta, GA (US)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/795,868

(22) PCT Filed: Jan. 17, 2006

(86) PCT No.: PCT/EP2006/001003

§ 371 (c)(1),
(2), (4) Date: Apr. 2, 2008

(87) PCT Pub. No.: WO2006/079562

PCT Pub. Date: Aug. 3, 2006

(65) Prior Publication Data

US 2009/0018367 A1 Jan. 15, 2009

(30) Foreign Application Priority Data

Jan. 25, 2005 (EP) .................. 05075184
Jan. 25, 2005 (EP) .................. 05075185

(51) Int. Cl.
*C07C 45/28* (2006.01)
(52) U.S. Cl. .................................... 568/342
(58) Field of Classification Search .................. 568/342
See application file for complete search history.

(56) References Cited

U.S. PATENT DOCUMENTS 4,238,415 A * 12/1980 Bryan ........................ 568/342

FOREIGN PATENT DOCUMENTS

EP  0 004 105 A  9/1979
EP  0 659 726 A  6/1995

OTHER PUBLICATIONS

International Search Report mailed Apr. 26, 2006 in PCT/EP2006/001003.
Written Opinion mailed Apr. 26, 2006 in PCT/EP2006/001003.

* cited by examiner

*Primary Examiner*—Sikarl A Witherspoon
(74) *Attorney, Agent, or Firm*—Nixon & Vanderhye P.C.

(57) ABSTRACT

The present invention relates to a process for preparing cyclohexanone and cyclohexanol, said process comprising (a) neutralising acids and/or carbon dioxide present in an organic solution further comprising cyclohexylhydroperoxide by mixing the organic solution with a first aqueous base solution at a temperature of from 50 to 80° C. to form a first mixture comprising a first aqueous phase with a pH of from 8.5 to 13 and a first organic phase, (b) separating first aqueous phase from the first mixture resulting in a remaining mixture comprising first organic phase, (c) decomposing cyclohexylhydroperoxide present in said remaining mixture by mixing said remaining mixture with a second aqueous base solution at a temperature of from 60 to 110° C. to form a second mixture comprising a second aqueous phase and a second organic phase comprising cyclohexanone and cyclohexanol, (d) separating the second aqueous phase from the second organic phase at a temperature higher than 80° C.

12 Claims, 1 Drawing Sheet

PROCESS FOR PREPARING CYCLOHEXANONE AND CYCLOHEXANOL

This application is the US national phase of international application PCT/EP2006/001003 filed 17 Jan. 2006 which designated the U.S. and claims benefit of EP 05075184.1 and EP 05075185.8, dated 25 Jan. 2005 and 25 Jan. 2005, the entire content of which is hereby incorporated by reference.

The present invention relates to a process for preparing cyclohexanone and cyclohexanol, said process comprising
(a) neutralising acids and/or carbon dioxide present in an organic solution further comprising cyclohexylhydroperoxide by mixing the organic solution with a first aqueous base solution to form a first mixture comprising a first aqueous phase and a first organic phase,
(b) separating first aqueous phase from the first mixture resulting in a remaining mixture comprising first organic phase,
(c) decomposing cyclohexylhydroperoxide present in said remaining mixture by mixing said remaining mixture with a second aqueous base solution to form a second mixture comprising a second aqueous phase and a second organic phase comprising cyclohexanone and cyclohexanol,
(d) separating the second aqueous phase from the second organic phase.

Such a process is for example described in EP-A-4105. In the process as described in EP-A-4105 a mixture obtained by oxidation of cyclohexane and comprising cyclohexylhydroperoxide, acids and carbon dioxide is subjected to a neutralization to neutralize the acids and carbon dioxide present in such oxidation mixture by addition of an aqueous base solution, resulting in a mixture comprising an aqueous phase and an organic phase. The neutralization takes place at a temperature of between 80-170° C., preferably between 130-160° C. The pH of the aqueous phase is higher than 7 at 25° C., preferably 8 to 13. After the neutralization, the aqueous phase is separated off and the resulting organic solution is subjected to a decomposition to decompose cyclohexylhydroperoxide into cyclohexanone and cyclohexanol. The decomposition takes place at a temperature of between 80-170° C. EP-A-4105 describes that, after completion of the decomposition reaction, the resulting aqueous layer can be separated off and cyclohexanone and cyclohexanol can be isolated from the resultant organic solution by means of distillation.

It has been found that in the process of EP-A-4105 the selectivity into cyclohexanone and cyclohexanol is low. It has further been found that separating aqueous phase from the mixture, obtained after completion of the decomposition reaction, is difficult to carry out. It has also surprisingly been found that the process as described in EP-A-4105 may result in fouling and/or byproduct formation in distillation column(s) in which organic solution obtained in the decomposition is distilled.

Accordingly, it is a goal of the invention to improve the selectivity into cyclohexanone and cyclohexanol and at the same time improve the separation of the mixture obtained after decomposition.

This object is achieved by effecting the neutralising at a temperature of from 50 to 80° C. and at a pH of the first aqueous phase of from 8.5 to 13, effecting the decomposing at a temperature of from 60 to 110° C. and effecting the separating of the mixture obtained after decomposing at a temperature higher than 80° C. It has now been found that said neutralizing may also take place at a temperature from 50 to 80° C. without negatively influencing the process for preparing cyclohexanone and cyclohexanol and in particular without negatively influencing the process for neutralising acids and/or carbon dioxide present in an organic solution further comprising cyclohexylhydroperoxide.

Accordingly, the present invention provides a process for preparing cyclohexanone and cyclohexanol, said process comprising
(a) neutralising acids and/or carbon dioxide present in an organic solution further comprising cyclohexylhydroperoxide by mixing the organic solution with a first aqueous base solution at a temperature of from 50 to 80° C. to form a first mixture comprising a first aqueous phase with a pH of from 8.5 to 13 and a first organic phase,
(b) separating first aqueous phase from the first mixture resulting in a remaining mixture comprising first organic phase,
(c) decomposing cyclohexylhydroperoxide present in said remaining mixture by mixing said remaining mixture with a second aqueous base solution at a temperature of from 60 to 110° C. to form a second mixture comprising a second aqueous phase and a second organic phase comprising cyclohexanone and cyclohexanol,
(d) separating the second aqueous phase from the second organic phase at a temperature higher than 80° C.

An additional advantage of the process according to the invention is an improved selectivity to cyclohexanone and cyclohexanol obtained in the process of the invention.

Preferably, said neutralising is carried out at a temperature from 55 to 70° C.

Preferably, the pH of the first aqueous phase is higher than 9, measured at 25° C. It has been found that a pH of the first aqueous phase higher than 9 (measured at 25° C.), results in an significant improvement of the separating of the second aqueous phase from the mixture obtained after completion of the decomposition reaction, resulting in decreased sodium content in the second organic phase. It has been found that a reduced sodium content in the second organic phase results in less fouling, for example due to salt precipitation, and/or byproduct formation, for example due to aldol condensation, in distillation column(s) in which remaining mixture comprising second organic phase is distilled. There is no specific upper limit for the pH of the first aqueous phase. However, an increased pH of the first aqueous phase results in an increased base consumption. Therefore, the pH of the first aqueous phase is preferably lower than 13, more preferably lower than 11 and even more preferably lower than 10.5. Most preferably, the pH of the first aqueous phase is from 9 to 10. The pH of the first aqueous phase may be adjusted by any suitable method. A preferred method is mixing the organic solution comprising cyclohexylhydroperoxide and acids and/or carbon dioxide with such a quantity of first aqueous base solution that the pH of the first aqueous phase has the desired value.

Said decomposing is preferably effected at a temperature of between 70 to 110° C., more preferably at a temperature of between 80 and 110° C.

Separating the second aqueous phase from the second organic phase is preferably carried out at a temperature higher than 85° C. and more preferably at a temperature higher than 90° C. Separating the second aqueous phase from the second organic phase at increased temperature results in an increase of the efficiency of the separating. Preferably, separating the second aqueous phase from the second organic phase is carried out at the outlet temperature of the last decomposition reactor.

The second mixture obtained in said decomposing comprises a second aqueous phase and a second organic phase comprising cyclohexanone and cyclohexanol. The process of the invention further comprises separating the second aqueous phase from the second organic phase. Preferably, said separating is carried out such that after said separating the sodium content in the second organic phase is less than 100 ppm, more preferably less than 50 ppm and even more preferably less than 10 ppm (relative to the second organic phase). It has surprisingly been found that the pH of the first aqueous phase has a significant effect on the separating of the second aqueous phase from the mixture obtained after completion of the decomposition reaction. Said separating may be effected by any operation known to one skilled in the art for separating aqueous phase from organic phase, for example decantation and/or making use of plate separators or of electrostatic separators. In a preferred embodiment, said separating is effected using one or more gravity settlers followed by a plate separator.

In the process of the invention, neutralising acids and/or carbon dioxide present in an organic solution further comprising cyclohexylhydroperoxide is effected by mixing the organic solution with a first aqueous base solution. Said mixing may be effected by any suitable method, for example by using a packed column, a flow or line mixer, a pump, a static mixer, an agitated vessel or combinations thereof. Mixing may also involve injecting the first aqueous base solution into the organic solution.

The first mixture obtained in said neutralizing comprises a first aqueous phase comprising neutralized acids and a first organic phase comprising cyclohexylhydroperoxide. The process of the invention further comprises separating first aqueous phase from the first mixture resulting in a remaining mixture comprising first organic phase. Said separating may be effected by any suitable method, for example by decantation making use of one or more gravity settlers.

Preferably, the process of the invention further comprises discharging at least a portion of the first aqueous phase (the purge). In one embodiment, the process of the invention comprises separating first aqueous phase from first organic phase, discharging a portion of the separated first aqueous phase and feeding another portion of the separated first aqueous phase, preferably the remaining first aqueous phase, to the decomposition. In another embodiment, the process of the invention comprises separating a portion of the first aqueous phase from the first organic phase resulting in a separated first aqueous phase and in a remaining mixture comprising first organic phase and the other portion of the first aqueous phase, discharging the separated first aqueous phase and feeding the remaining mixture to the decomposition.

In the process of the invention, decomposing cyclohexylhydroperoxide present in said remaining mixture is effected by mixing said remaining mixture with the second aqueous base solution to form a second mixture comprising a second aqueous phase and a second organic phase comprising cyclohexanone and cylohexanol. Said mixing may be effected by any suitable method, for example by using a packed column, a flow or line mixer, a pump, a static mixer, an agitated vessel or combinations thereof. Mixing may also involve injecting the second aqueous base solution into the remaining mixture. In a preferred embodiment, decomposing is effected in a reaction zone with plug flow characteristics, for example an in-line mixer or several continuous stirred-tank reactors in series.

Preferably, said decomposing is effected in the presence of a water soluble metal salt catalyst that catalyses decomposition of cyclohexylhydroperoxide into cyclohexanone and cyclohexanol, for instance salts of transition metals, such as cobalt, chromium, nickel, iron, manganese and copper. Preference is given to effecting the decomposing with, as transition metal salt, a salt of cobalt and/or of chromium, for instance a sulphate or nitrate. The concentration of the water-soluble metal salt may differ within wide ranges, for instance a concentration of from 0.1 to 100 ppm (calculated as metal and relative to the weight of the aqueous phase). Preferably, a concentration of from 1 to 10 ppm is applied.

The first and second aqueous base solutions refer to aqueous solutions comprising dissolved base(s). Preferably, the base is an earth alkali metal hydroxide and/or one or more salts of an earth alkali metal or the base is an alkali metal hydroxide and/or one or more salts of an alkali metal. Hence, the first and second aqueous base solutions are preferably aqueous solutions comprising an earth alkali metal hydroxide and/or one or more salts of an earth alkali metal or the aqueous base solutions are aqueous solutions comprising an alkali metal hydroxide and/or one or more salts of an alkali metal. More preferably, the first and second aqueous base solutions are aqueous solutions comprising an alkali metal hydroxide and/or one or more salts of an alkali metal. Suitable (earth) alkali metal salts are (earth) alkali metal phosphates, (earth) alkali metal carbonates and (earth) alkali metal bicarbonates. Preferred (earth) alkali metal salts are (earth) alkali metal carbonates and (earth) alkali metal bicarbonates. A preferred earth alkali metal is magnesium. The alkali metal is preferably potassium or sodium, more preferably sodium. In a preferred embodiment, the first and second aqueous base solutions further comprise carboxylic acids salts. The presence of carboxylic acid salts results in an increased reaction velocity for decomposing cyclohexylhydroperoxide into the desired products cyclohexanone and cyclohexanol. Salts of mono- and polycarboxylic acids in which the carboxylic acid moiety preferably comprises 1-24 C-atoms are suitable, more preferably the carboxylic acid moiety comprises 1-12 C-atoms. Examples of suitable carboxylic acids are formic acid, acetic acid, propionic acid, butyric acid, pentanoic acid, hexanoic acid, heptanoic acid, stearic acid, decanoic acid, glutaric acid, adipic acid and heptane dicarboxylic acid. Special preference is given to the use of mixtures of different carboxylic acids, since these are simply obtainable. Preferably, the carboxylic acid salts concentration in the first and second aqueous base solutions is higher than 5 wt. %, more preferably higher than 10 wt. %. Preferably, the carboxylic acid salts concentration in the first and second aqueous base solutions is lower than the solubility limit of the carboxylic acid salts in the aqueous base solutions at the applied reaction conditions.

Preferably, the first aqueous base solution is an aqueous solution comprising an alkali metal carbonate, an alkali metal bicarbonate and alkali metal salts of carboxylic acids. More preferably, the first aqueous base solution is an aqueous solution comprising sodium carbonate, sodium bicarbonate and sodium salts of carboxylic acids. Preferably, the sum amount of acid salts, bicarbonate and carbonate of the first aqueous phase is lower than or equal to 40 wt. % and higher than or equal to 20 wt. % (relative to the first aqueous phase).

Preferably, the second aqueous base solution is an aqueous solution comprising an alkali metal hydroxide, preferably sodium hydroxide. More preferably, the second aqueous base solution is an aqueous solution comprising an alkali metal hydroxide, an alkali metal carbonate and alkali metal salts of carboxylic acids. Preferably, the sum amount of acid salts and carbonate of the second aqueous phase is lower than or equal to 40 wt. % and higher than or equal to 20 wt. % (relative to the second aqueous phase).

Preferably, the pH of the second aqueous phase is higher than 13, measured at 25° C. in order to obtain efficient decomposition of cyclohexylhydroperoxide. The pH of the second aqueous phase may be adjusted by any suitable method. A preferred method is adjusting the pH of the second aqueous phase by feeding such an amount of an aqueous solution of an alkali metal hydroxide to the decomposition that the pH of the second aqueous phase of the last decomposition reactor has the desired value.

The volume ratio of the second aqueous phase to the second organic phase is preferably higher than 0.01, more preferably higher than 0.02, more preferably higher than 0.05 and even more preferably higher than 0.1. Increasing the volume ratio of the aqueous phase to the organic phase results in increased decomposition reaction velocity. There is no specific upper limit for the volume ratio of the aqueous phase to the organic phase. A volume ratio of the aqueous phase to the organic phase higher than 1 may be used, but offer no particular advantage. Therefore, the volume ratio of the second aqueous phase to the second organic phase is preferably lower than 1, more preferably lower than 0.6. In a preferred embodiment, the remaining mixture comprising second organic phase is mixed with such a quantity of second aqueous base solution that the volume ratio of the second aqueous phase to the second organic phase has the desired value.

In a first and preferred embodiment, the process further comprises feeding a portion of the separated second aqueous phase to the neutralisation and feeding a portion of the separated second aqueous phase to the decomposition. In that case, the first and second aqueous base solution comprises a portion of the second aqueous phase obtained after said separating. The first and second aqueous base solution will then already contain carboxylic acid salts as mentioned above. The carboxylic acids can be formed as by-product in the decomposition, upon which owing to the presence of (earth) alkali metal, salts are formed with the carboxylic acids.

In a second and more preferred embodiment, the process further comprises, after said separating of the second aqueous phase from the second organic phase, dividing said separated second aqueous phase into two parts, feeding one part (part A) of said separated second aqueous phase to the neutralisation and feeding the other part (part B) of said separated second aqueous phase to the decomposition. Preferably, the first aqueous base solution is part A of said separated second aqueous phase; and a part of the second aqueous base solution is part B of said separated second aqueous phase and the other part of the second aqueous base solution being an aqueous solution of an alkali metal hydroxide. Preferably, the amount of aqueous solution of an alkali metal hydroxide fed to the decomposing is such that the pH of the second aqueous phase of the last decomposition reactor has the desired value. Preferably, the pH of the second aqueous phase is higher than 13, measured at 25° C. Preferably, the amount of the separated second aqueous phase fed to the neutralisation is such that the pH of the first aqueous phase is higher than 8.5 and lower than 13, more preferably higher than 9 and lower than 11 and even more preferably from 9 to 10, measured at 25° C. Preferably, the amount of the separated second aqueous phase fed to the decomposition is such that the volume ratio of the second aqueous phase to the second organic phase has the desired value. The volume ratio of the second aqueous phase to the second organic phase is preferably higher than 0.01 and preferably lower than 1. In said second embodiment, the process of the invention further comprises discharging at least a portion of the first aqueous phase (the purge). In one embodiment, the process of the invention comprises separating first aqueous phase from first organic phase, discharging a portion of the separated first aqueous phase and feeding another portion of the separated first aqueous phase, preferably the remaining first aqueous phase, to the decomposition. In another embodiment, the process of the invention comprises separating a portion of the first aqueous phase from the first organic phase resulting in a separated first aqueous phase and in a remaining mixture comprising first organic phase and the other portion of the first aqueous phase, discharging the separated first aqueous phase and feeding the remaining mixture to the decomposition. Preferably such a quantity of the first aqueous phase is separated from the first mixture and discharged that accumulation of water in the process is avoided.

The acids and/or carbon dioxide to be neutralized and the cyclohexylhydroperoxide to be decomposed according to the invention may be present in any organic solution comprising acids and cyclohexylhydroperoxide. For example, the organic solution comprising between 0.1 and 20 wt. % cyclohexylhydroperoxide and between 0.1 and 3 wt. % acids (relative to the organic solution).

The cyclohexylhydroperoxide and the acids which are present in the organic solution fed to said neutralizing can be obtained with various known processes.

Preparing the cyclohexylhydroperoxide and the acids, for example, involves oxidizing cyclohexane with an oxygen containing gas in the presence or absence of substances promoting the decomposition of the cyclohexylhydroperoxide formed resulting in an oxidation mixture comprising cyclohexane, cyclohexanone, cyclohexanol, cyclohexylhydroperoxide, acids, carbon dioxide, esters, low boiling compounds, and high boiling compounds. With low boiling compounds is meant organic compounds having a boiling point lower than cyclohexanone and higher than cyclohexane. Examples are butanol, pentanal, hexanal, pentanol and epoxy-cyclohexane. With high boiling compounds is meant organic compounds having a boiling point higher than cyclohexanol. Examples are 2-cyclohexylidene cyclohexanone, 2-hexylidene cyclohexanone and 2-(cyclohexen-1-yl)cyclohexanone. The oxidation usually takes place in the liquid phase. As oxygen-containing gas use can be made for instance of pure oxygen, air, rich or poor in oxygen, or oxygen mixed with nitrogen or another inert gas. Suitable oxidation temperatures are between 120 and 200° C. Preferably, an oxidation temperature between 140 and 190° C. is used. The oxidation reaction is usually carried out for 5 minutes to 24 hours. The pressure is usually between 0.3 and 5 MPa, preferably between 0.4 and 2.5 MPa.

Preferably, the cyclohexylhydroperoxide to be decomposed according to the invention is obtained by oxidation of cyclohexane with an oxygen-containing gas in the absence of substances promoting the decomposition of the cyclohexylhydroperoxide formed, such as compounds of transition metals, hereinafter referred to as uncatalysed cyclohexane oxidation. Uncatalysed cyclohexane oxidation is preferred to catalysed cyclohexane oxidation because uncatalysed cyclohexane oxidation results in higher yields of cyclohexylhydroperoxide. As a rule, the mixture obtained in such uncatalysed cyclohexane oxidation comprises a weight percentage of cyclohexylhydroperoxide that is at least comparable to the weight percentages of cyclohexanone and cyclohexanol. Often, the amount of cyclohexylhydroperoxide in the mixture obtained in such uncatalysed cyclohexane oxidation is at least two times as large as the amount of cyclohexanone and cyclohexanol. In contrast to the uncatalysed cyclohexane oxidation, the catalysed oxidation—where cobalt and/or chromium compounds are usually applied—cyclohexanol and cyclohexanone are the main products formed, besides a relatively small amount of cyclohexylhydroperoxide, a large portion of the cyclohexylhydroperoxide being already decomposed to cyclohexanol during the oxidation. The catalysed oxidation yields a mixture that contains less than 50% cyclohexylhydroperoxide relative to the weight percentage of cyclohexanol+cyclohexanone. This is often even less than 40% peroxide compared with the weight percentage of cyclohexanol+ cyclohexanone. Notwithstanding this, the process according to the invention may also advantageous be applied for decomposing cyclohexylhydroperoxide obtained by catalysed oxidation.

Optionally, prior to subjecting the acids and/or carbon dioxide, present in a reaction mixture obtained by oxidation of cyclohexane with an oxygen-containing gas, to said neutralizing, the mixture obtained by oxidation of cyclohexane with an oxygen-containing gas can be concentrated by separating, preferably by flashing or distilling, all or preferably part of the cyclohexane.

Preferably, the process further comprises, prior to said neutralizing, degassing of entrained and/or dissolved gasses present in the organic solution.

In case the organic solution comprising cyclohexylhydroperoxide and acids and/or carbon dioxide originates from cyclohexane oxidation, the organic solution usually also comprises other compounds, for example (1) cyclohexane and/or (2) cyclohexanone and/or (3) cyclohexanol. The cyclohexylhydroperoxide concentration, the carbon dioxide concentration and the acids concentration in the organic solution is not critical. The cyclohexylhydroperoxide and acids may for example be present in an organic solution comprising between 0.1 and 20 wt. % cyclohexylhydroperoxide and between 0.1 and 3 wt. % (relative to the organic solution). The sum concentration of cyclohexanone and cyclohexanol in the organic solution is not critical and is for instance between 0 and 20 wt. % (relative to the total organic solution).

The process of the invention preferably further comprises distilling the second organic phase, if so desired after washing with water, to obtain cyclohexanone and cyclohexanol.

In a preferred embodiment, the present invention provides a process for the preparation of cyclohexanone and cyclohexanol, said process comprising
(1) Oxidizing cyclohexane with an oxygen-containing gas to obtain an organic solution comprising cyclohexylhydroperoxide, cyclohexane, cyclohexanol, cyclohexanone, acids, carbon dioxide, esters, low boiling compounds and high boiling compounds;
(2) Optionally, separating part of the cyclohexane from said organic solution;
(3) Neutralizing acids and carbon dioxide formed in the oxidation by mixing the organic solution with a first aqueous base solution to form a first mixture comprising a first aqueous phase and a first organic phase;
(4) Separating first aqueous phase from the first mixture resulting in a remaining mixture comprising first organic phase;
(5) Decomposing cyclohexylhydroperoxide present in said remaining mixture by mixing said remaining mixture with a second aqueous base solution to form a second mixture comprising a second aqueous phase and a second organic phase comprising cylohexanone and cyclohexanol,
(6) Separating the second aqueous phase from the second organic phase;
(7) Distilling the second organic phase to obtain cyclohexanone and cyclohexanol.

In this preferred embodiment, distilling the second organic phase to obtain cyclohexanone and cyclohexanol preferably comprises the following steps: separating cyclohexane from the second organic phase (7.a), separating low boiling compounds from the second organic phase (7.b), separating cyclohexanone from the second organic phase (7.c) and separating cyclohexanol from the second organic phase (7.d). Other purification and/or recovery steps may be carried out between (7.a), (7.b), (7.c) and/or (7.d).

More preferably, in this preferred embodiment, distilling the second organic phase to obtain cyclohexanone and cyclohexanol comprises separating, by distillation, cyclohexane from the second organic phase to obtain a top product comprising cyclohexane and a first bottom product comprising cyclohexanone, cyclohexanol, low boiling compounds and high boiling compounds;

separating, by distillation, low boiling compounds from the first bottom product to obtain a top product comprising low boiling compounds and a second bottom product comprising cyclohexanone, cyclohexanol and high boiling compounds; and separating, by distillation, cyclohexanone from the second bottom product to obtain a top product comprising cyclohexanone and a third bottom product comprising cyclohexanol and high boiling compounds; and separating, by distillation, cyclohexanol from the third bottom product to obtain a top product comprising cyclohexanol and a bottom product comprising high boiling compounds. Cyclohexanol may subsequently be subjected to a dehydrogenation reaction. Other purification and/or recovery steps may be carried out between the above mentioned distillation steps.

DESCRIPTION OF AN EMBODIMENT

Figure 1:
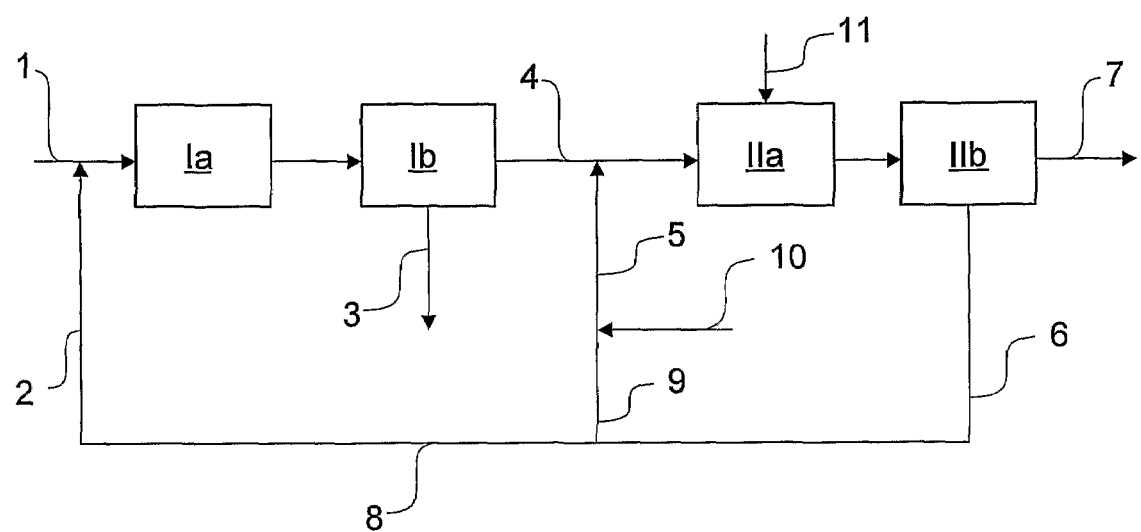
FIG. 1 represents a preferred embodiment of the process according to the invention. In this FIGURE, the symbols have the following meaning:
(1)=organic solution
(2)=first aqueous base solution
(3)=first aqueous phase
(4)=remaining mixture comprising first organic phase
(5)=second aqueous base solution
(6)=second aqueous phase
(7)=second organic phase
(8)=part A
(9)=part B
(10)=aqueous solution of an alkali metal hydroxide
(11)=aqueous solution of a water-soluble transition metal salt catalyst
Ia=neutralisation reactor(s)
Ib=liquid/liquid separator(s)
IIa=decomposition reactor(s)
IIb=liquid/liquid separator(s)

Referring to FIG. 1, Ia represents a neutralisation reactor. Line 1 represents an organic solution comprising acids, carbon dioxide and cyclohexyllhydroperoxide. Line 2 represents a first aqueous base solution, which is a part (part A) of the second aqueous phase (line 6) obtained in the separator (the last separator in case the separating of the mixture obtained in the decomposition involves more than one separator). The organic solution is pre-mixed with the first aqueous base solution before being fed to neutralisation reactor la. After neutralising the first mixture comprising a first aqueous phase and a first organic phase is supplied to liquid/liquid separator Ib, where first aqueous phase and first organic phase are separated. A portion of the separated first aqueous phase is discharged through line 3. The remaining mixture (line 4) comprising organic phase and the other portion of the first aqueous phase is pre-mixed with the second aqueous base solution (line 5) before being fed to decomposition reactor ha (the first decomposition reactor in case the decomposing is effected in a series of decomposition reactors). The second aqueous base solution is obtained by mixing a part (part B) (line 9) of the second aqueous phase (line 6) obtained in the separator (the last separator in case the separating of the mixture obtained in the decomposition involves more than one separator) with an aqueous solution of an alkali metal hydroxide (line 10), preferably sodium hydroxide. An aqueous solution of a water-soluble transition metal salt catalyst is fed to decomposition reactor IIa through line 11. In case the decomposing is effected in a series of decomposition reactors, the above-mentioned streams are fed to the first decomposition reactor. After decomposing, the second mixture comprising the second aqueous phase and the second organic phase is supplied to liquid/liquid separator IIb (the first separator in case the separating of the mixture obtained in the decomposition involves more than one separator), where the second aqueous phase (line 6) is separated from the second organic phase (line 7). The second organic phase (line 7) is distilled, optionally after washing with water, to obtain cyclohexanone and cyclohexanol.

The invention will be elucidated by the following examples without being limited thereto.

Example 1

An oxidation mixture (line 1 in FIG. 1), obtained from an uncatalyzed cyclohexane oxidation, consisted of cyclohexane, 3.2 wt. % cyclohexylhydroperoxide, 0.5 wt. % cyclohexanol, 0.3 wt. % cyclohexanone and by-products. Among other by-products, this mixture also contained 0.02 wt. % $CO_2$ and 0.4 wt. % mixed organic acids (mono and di-acids ranging from C1 to C6). The oxidation mixture was cooled to 60° C. Before being fed to a well-stirred neutralization reactor (Ia in FIG. 1), the cooled oxidation mixture was pre-mixed with an aqueous base solution (line 2 in FIG. 1) obtained from the plate separator after the cyclohexylhydroperoxide decomposition reactors. The aqueous base solution (line 2) contained 4.1 wt % $Na_2CO_3$, 1.4 wt % NaOH and 14.6 wt. % sodium-carboxylates of mixed monoacids and di-acids ranging from C1 to C6 acids. Both aqueous and organic solutions were thoroughly mixed in the neutralization reactor (Ia) to obtain a fine organic-aqueous emulsion. The aqueous phase content in this emulsion was 3.8 vol. %. At the outlet of this reactor, $CO_2$ and organic acids were quantitatively neutralized. The temperature at the outlet of the neutralisation reactor was 65° C. After this reactor, the emulsion was supplied to a gravity settler (Ib in FIG. 1) in which aqueous phase is separated from the emulsion. The resulting aqueous phase contained 0.3 wt. % $Na_2CO_3$, 3.6 wt. % $NaHCO_3$ and 21.5 wt. % Na-carboxylates of mixed monoacids and di-acids ranging from C1 to C6 acids (No NaOH). The amount of stream 2 was chosen such that the pH of the aqueous phase leaving the gravity settler was 9.1. The amount of the aqueous phase purged (line 3 in FIG. 1) was 65% of the aqueous phase leaving the gravity-settler. Thus, 35% of the aqueous phase leaving the gravity settler was united with the separated organic phase (line 4 in FIG. 1). The resulting mixture (line 4) was pre-mixed with an aqueous base solution (line 5) before being fed to the first well-stirred decomposition reactor IIa. The aqueous base solution (line 5) was obtained by mixing a part (line 9) of the aqueous base solution (line 6 in FIG. 1) obtained from the plate separator after the cyclohexylhydroperoxide decomposition reactors with an aqueous NaOH solution (line 10). An additional aqueous NaOH solution (line 10) was fed to stream 9 to replenish the consumed base in the neutralization and decomposition process. The amount of NaOH fed was such that the NaOH concentration in the aqueous phase at the outlet of the last decomposition reactor was 0.4 mol/liter. Also a small amount of aqueous solution containing cobalt sulphate (line 11 in FIG. 1) was added to the first decomposition reactor as catalyst for the decomposition of cyclohexylhydroperoxide to cyclohexanol and cyclohexanone. The concentration of cobalt in the aqueous phase present in the decomposition reactors was approx. 5 ppm. After the last decomposition reactor the cyclohexylhydroperoxide conversion was complete. Due to the adiabatic temperature rise, the temperature at the outlet of the last decomposition reactor was 95° C. The obtained emulsion at the outlet of this reactor was allowed to settle (IIb in FIG. 1) in 2 consecutive gravity-settlers followed by a plate-separator. After L/L separation the sodium content of the resulting organic phase (line 7 in FIG. 1) was less than 5 ppm, demonstrating an effective removal of the aqueous phase. The separated organic phase comprised mainly cyclohexane and further 1.7 wt. % cyclohexanone and 1.7 wt. % cyclohexanol. This corresponded to a selectivity of the cyclohexylhydroperoxide decomposition reaction of 91.5%. The aqueous phase from the L/L separators after the decomposition reactors was largely recycled to the first decomposition reactor (line 9 in FIG. 1). The size of this stream was controlled such that the decomposition reactors contained approx. 15 vol. % of aqueous phase. A minor part of the aqueous phase from the L/L separators after the decomposition reactors was fed to the feed of the neutralization reactor (line 8 of FIG. 1). In this experiment the total NaOH consumption was 96 kg per ton of produced cyclohexanone+cyclohexanol.

Comparative Experiment A

Example 1 was repeated, with the difference that the size of stream 2 was adjusted such that the pH of the aqueous phase at the outlet of the neutralization reactor Ia was 8.3. Also in this experiment stream 9 was controlled such that the emulsion obtained in the decomposition reactors contained approx. 15 vol. % aqueous phase and stream 10 and 11 were controlled in a way that in the aqueous phase at the outlet of the last decomposition reactor the NaOH and cobalt content was 0.4 mol/liter and 5 ppm respectively. The conversion of cyclohexylhydroperoxide was complete and the selectivity of the decomposition reaction was 91.5%. In this experiment it appeared that the separation of the aqueous and organic phases became slightly worse compared to Example 1 and it became more difficult to maintain the process on the desired process conditions. This also caused the sodium content in organic product stream 8 to fluctuate between approx. 5 and 20 ppm. In this experiment the total NaOH consumption was 95 kg per ton of produced cyclohexanone+cyclohexanol.

Comparative Experiment B

Example 1 was repeated with the difference that the size of stream 2 was adjusted such that that the pH of the aqueous phase at the outlet of the neutralization reactor Ia was pH=7.5. Also in this case we aimed for 15 vol % of aqueous phase (with 5 ppm Cobalt and 0.4 mol NaOH/liter) at the total outlet of the last decomposition reactor. However the process became highly unstable due to the formation of more stable emulsions which were more difficult to separate. Although cyclohexylhydroperoxide conversion was still complete, we observed strong fluctuations in the sodium content of Stream 7. The average sodium content was >100 ppm and this mode of operation had to be abandoned because of unfavorable effects in downstream operations (fouling and yield-loss in reboilers).

Comparative Experiment C

Example 1 was repeated with the difference that the oxidation mixture (Stream 1) was cooled to 95° C. The size of stream 2 was adjusted such that the pH of the aqueous phase at the outlet of the neutralization reactor Ia was 9.1. Also in this experiment stream 9 was controlled such that the emulsion obtained in the decomposition reactors contained approx. 15 vol % aqueous phase and stream 10 and 11 were controlled in a way that in the aqueous phase at the outlet of the last decomposition reactor the NaOH and cobalt content was 0.4 mol/liter and 5 ppm respectively. The conversion of cyclohexylhydroperoxide was complete and the selectivity of the decomposition reaction was 87.6%. Similar good phase separation was obtained as in Experiment 1. The sodium content in Stream 8 was less than 5 ppm. In this experiment the total NaOH consumption was 112 kg per ton of produced cyclohexanone/cyclohexanol.

The invention claimed is:

1. Process for preparing cyclohexanone and cyclohexanol, said process comprising
   (a) neutralising acids and/or carbon dioxide present in an organic solution further comprising cyclohexylhydroperoxide by mixing the organic solution with a first aqueous base solution at a temperature of from 55 to 70° C. to form a first mixture comprising a first aqueous phase with an adjusted pH of from 8.5 to 13 and a first organic phase,
   (b) at least partially separating the first aqueous phase from the first mixture resulting in a remaining mixture comprising first organic phase,
   (c) decomposing cyclohexylhydroperoxide present in the remaining mixture by mixing the remaining mixture with a second aqueous base solution at a temperature of from 60 to 110° C. to form a second mixture comprising a second aqueous phase and a second organic phase comprising cyclohexanone and cyclohexanol,
   (d) separating the second aqueous phase from the second organic phase at a temperature higher than 80° C.

2. Process according to claim 1, wherein separating of the second aqueous phase from the second organic phase according to step (d) is carried out at a temperature higher than 90° C.

3. Process according to claim 1, wherein the adjusted pH of the first aqueous phase is higher than 9 and lower than 13, measured at 25° C.

4. Process according to claim 1, wherein the adjusted pH of the first aqueous phase is from 9 to 10, measured at 25° C.

5. Process according to claim 1, wherein the pH of the second aqueous phase is adjusted to a pH higher than 13, measured at 25° C.

6. Process according to claim 1, further comprising (e1) feeding a first portion of the second aqueous phase separated according to step (d) to the neutralizing step (a) and (e2) feeding a second portion of second aqueous phase separated according to step (d) to the decomposing step (c).

7. Process according to claim 1, further comprising (e) dividing the second aqueous phase separated according to step (d) into parts (A) and (B), respectively, and (f) feeding the part (A) of the divided second aqueous phase to the neutralizing step (a) and feeding the part (B) of the divided second aqueous phase to the decomposing step (c).

8. Process according to claim 7, wherein the first aqueous base solution is part (A) of the separated second aqueous phase, and wherein a part of the second aqueous base solution is part (B) of the separated second aqueous phase and another part of the second aqueous base solution is an aqueous solution of an alkali metal hydroxide.

9. Process according to claim 6, wherein the separated second aqueous phase fed to the neutralizing step (a) is in an amount such that the pH of the first aqueous phase is adjusted to a pH higher than 8.5, measured at 25° C.

10. Process according to claim 6, wherein the separated second aqueous phase fed to the neutralizing step (a) is in an amount such that the pH of the first aqueous phase is from 9 to 10, measured at 25° C.

11. Process according to claim 1, further comprising the step of distilling the remaining mixture comprising second organic phase to obtain cyclohexanone and cyclohexanol.

12. Process according to claim 1, wherein the neutralizing step (a) is practiced at a temperature of about 65° C.

* * * * *